US010160947B2

(12) United States Patent
Bourdat et al.

(10) Patent No.: US 10,160,947 B2
(45) Date of Patent: Dec. 25, 2018

(54) DEVICE FOR LYSING BIOLOGICAL SPECIES AND METHOD IMPLEMENTED BY SAID DEVICE (71) Applicant: COMMISSARIAT A L'ENERGIE ATOMIQUE ET AUX ENERGIES ALTERNATIVES, Paris (FR)

(72) Inventors: Anne-Gaelle Bourdat, Nantoin (FR); Antonio Viana, Herbeys (FR); Remco Den Dulk, Saint-Egrève (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 217 days.

(21) Appl. No.: 15/313,740

(22) PCT Filed: May 27, 2015

(86) PCT No.: PCT/IB2015/053970
§ 371 (c)(1),
(2) Date: Nov. 23, 2016

(87) PCT Pub. No.: WO2015/181743
PCT Pub. Date: Dec. 3, 2015

(65) Prior Publication Data
US 2017/0218326 A1 Aug. 3, 2017

(30) Foreign Application Priority Data
May 28, 2014 (FR) ...................................... 14 54866

(51) Int. Cl.
G01N 1/00 (2006.01)
C12N 1/06 (2006.01)
(Continued)

(52) U.S. Cl.
CPC ............. C12N 1/066 (2013.01); C12M 33/00 (2013.01); C12M 39/00 (2013.01); C12M 47/06 (2013.01);
(Continued)

(58) Field of Classification Search
CPC ........................................................ G01N 1/00
See application file for complete search history.

(56) References Cited

U.S. PATENT DOCUMENTS 3,941,317 A 3/1976 Kanor
5,114,858 A 5/1992 Williams et al.
(Continued)

FOREIGN PATENT DOCUMENTS

FR 2 781 500 A1 1/2000
WO 99/02958 A1 1/1999

OTHER PUBLICATIONS

International Search Report dated Aug. 25, 2015, issued in corresponding International Application No. PCT/IB2015/053970, filed May 27, 2015, 5 pages.
(Continued)

Primary Examiner — Jyoti Nagpaul
(74) Attorney, Agent, or Firm — Christensen O'Connor Johnson Kindness PLLC (57) ABSTRACT A device and method for lysing biological species present in a fluid includes implementing a rough surface against which the objects to be lysed are crushed by a shearing motion. A device for mechanically lysing biological species has a first and second wall mounted movable relative to each other, between an initial position in which the walls are separated from each other, and a lysing position in which the first wall presses against the second wall. The first and second walls also are mounted shearingly movable relative to each other in the lysing position. At least one of the first or second walls
(Continued)

has a rough bearing surface against the other wall and has a mean surface roughness parameter Ra of between 0.2 μm and 10 μm, and preferably between 0.2 μm and 3 μm.

18 Claims, 3 Drawing Sheets

(51) Int. Cl.
    *C12M 1/00*     (2006.01)
    *G01N 1/28*     (2006.01)
    *C12M 1/26*     (2006.01)

(52) U.S. Cl.
    CPC ............ *C12M 47/08* (2013.01); *G01N 1/286* (2013.01); *G01N 2001/2866* (2013.01)

(56) References Cited

U.S. PATENT DOCUMENTS

| | | |
|---|---|---|
| 6,358,474 B1 | 3/2002 | Dobler et al. |
| 6,632,662 B1 | 10/2003 | Broyer et al. |
| 2003/0066915 A1 | 4/2003 | Taylor |

OTHER PUBLICATIONS

Written Opinion dated Aug. 25, 2015, issued in corresponding International Application No. PCT/IB2015/053970, filed May 27, 2015, 6 pages.
Written Opinion of the International Searching Authority dated Aug. 25, 2015, issued in corresponding International Application No. PCT/IB2015/053970, filed May 27, 2015, 5 pages.
International Preliminary Report on Patentability dated Nov. 29, 2016, issued in corresponding International Application No. PCT/IB2015/053970, filed May 27, 2015, 1 page.

DEVICE FOR LYSING BIOLOGICAL SPECIES AND METHOD IMPLEMENTED BY SAID DEVICE

The invention relates to a device for lysing biological species (microorganisms, bacteria, cells, spores, etc.) and to a method implemented by this device.

The lysis of biological cells is necessary to collect and examine intracellular material. For example, cell lysis is needed to recover DNA from a cell for replication and analysis such as a DNA comparison.

The methods conventionally used for the lysis of biological species are the following.

Chemical lysis: this technique comprises the contacting of the cells with a lysis solution generally containing a detergent to cause disruption of the cells. This technique is efficient but may be hazardous for some cell materials. In addition, it is lengthy and requires numerous handling operations including a step to purify the lysis solution and optionally to concentrate the lysate, which is time consuming and carries the risk of losing a large amount of biological material at the time of purification and concentration and requires the skills of a specialised person: this technique is not efficient for the lysis of spores.

Lysis via heat shock: this technique comprises incubation of the extract for example at a temperature lower than 0° C., immediately followed by incubation of the extract at a temperature of at least 95° C., preferably about 100° C. This technique requires complex equipment in particular if it is desired to lyse spores.

Lysis via electrical field: this technique comprises the use of a potential difference leading to rupture of the cell membrane. This technique requires the use of complex equipment and, like the preceding methods, is scarcely adapted for the lysis of spores.

Mechanical lysis: this technique is based on agitation of the extract in the presence of beads so that the impacting of the beads against the cells leads to disruption thereof. This technique requires complex equipment. In addition, it is necessary to use beads fully free of microorganisms and they must be recovered after lysis. Examples of devices using this method are biological sample grinders in the Precellys© range by Bertin Technologies. These are expensive, cumbersome devices difficult to integrate into a compact instrument.

Lysis via pressure: this technique comprises application of hydrostatic pressure to the cells, leading to rupture of their membrane. This technique requires complex equipment.

Among the lysis methods using mechanical grinding, mention can be made of the following documents:

FR 2 781 500 which describes a method for mechanical lysis of microorganisms by setting in movement grinding means using a magnetic field; and US 2003/0066915 which describes a method for mechanical lysis of microorganisms by setting in movement grinding means using ultrasound.

Documents WO-A1-99/02958 and U.S. Pat. No. 5,114,858 each disclose a device for the mechanical lysis of biological species comprising a first and second wall, movable relative to one another between an initial position in which they are drawn apart and a lysis position in which the first wall forming a piston bears against the second wall, the first and second walls being mounted movable under shear relative to one another in the lysis position. The pistons presented in these two documents are provided with macroscopic projections which form grinding teeth and therefore do not impart microroughness to the corresponding bearing surfaces of these pistons.

All these techniques are complex and require extensive equipment. In addition, they require lengthy preparation and a lysis time of several tens of seconds to several minutes. Also, they are difficult to integrate in portable compact instruments.

The objective of the present invention is therefore to propose a device and method for the lysis of biological species that is simple, low-cost and can easily be integrated in laboratory equipment or in a portable device, and which has high lysis efficacy in particular on spores allowing satisfactory lysis (at least 50% of lysed biological species) in less than 10 seconds, even within 1 second.

For this purpose, the invention proposes a device and method for mechanical lysis using a rough surface against which the objects to be lysed are ground via frictional movement (shearing) and not via impacting or mere pressure.

The subject of the invention is therefore a device for the mechanical lysis of biological species contained in a fluid, comprising a first wall and a second wall mounted movable relative to one another, between an initial position in which the first and second walls lie distant from each other, and a lysis position in which the first wall presses against the second wall, the first and second walls also being mounted movable under shear relative to one another in the lysis position, characterized in that at least one of the first and second walls has a rough bearing surface against the other wall and has an average surface roughness parameter Ra of between 0.2 µm and 10 µm and preferably between 0.2 µm and 3 µm.

According to other embodiments of the device of the invention:

(i) one among the first wall and second wall can be a microporous wall i.e. porous to liquids and non-porous to biological species that are to be lysed;

(ii) the microporous wall may have a mean pore diameter of less than 1 µm, even less than 0.2 µm;

(iii) the microporous wall may be rough;

(iv) the rough microporous wall may be formed of a layer of microporous material having a planar surface on which a rough layer is positioned intended to bear against the other wall in lysis position;

(v) according to one variant of (iv), the rough microporous wall may be formed of a layer of microporous material having a rough surface;

(vi) according to another variant of (iv), the rough microporous wall may be formed of a layer of macroporous material having a rough surface on which a microporous layer is positioned intended to bear against the other wall in lysis position, the microporous layer being sufficiently flexible and thin to follow the contour of the surface roughness of the layer in macroporous material in lysis position;

(vii) the microporous wall may be non-rough and have an average surface roughness parameter Ra of less than 0.1 µm, whereas the non-microporous wall may be rough and have an average surface roughness parameter Ra of between 0.2 µm and 10 µm, preferably between 0.2 µm and 3 µm;

(viii) according to one variant of (vii), the first wall and the second wall may be rough;

(ix) the device of the invention may further comprise a chamber and a piston mounted mobile in the chamber between the initial position and the lysis position, the first wall being mounted on the mobile piston and the second wall being arranged facing the first wall;

(x) the second wall of the device may then be microporous, and the chamber may also comprise a fluid outlet arranged opposite the first wall relative to the second microporous wall;

(xi) the chamber may then further comprise a fluid inlet and another fluid outlet; and (xii) the chamber may then also comprise an impervious membrane arranged between the first wall, the fluid inlet and fluid outlet, the membrane being sufficiently thin and flexible to follow the contour of the roughness of at least one from among the first wall and second wall in lysis position.

The invention also relates to a method for the mechanical lysis of biological species comprising the following steps:

A) Providing a device such as afore-cited so that the first and second walls are in initial position;

B) Placing the biological species to be lysed between these walls;

C) Bringing the walls to lysis position;

D) Generating shear between these walls in lysis position to cause mechanical lysis of these species and obtain a lysate;

E) Drawing the walls away from each other until they lie in initial position; and F) Collecting the lysate of the biological species.

The method the invention is efficient since it allows a yield at least equivalent to the reference method for spore lysis using Precellys© grinders (Bertin).

The method is rapid compared with the reference method (Precellys© grinders (Bertin)): in less than 10 seconds compared with 30 seconds for the reference grinder.

The method of the invention is economical and direct since it requires neither the addition of any chemical substance, nor subsequent purification nor the addition of foreign bodies to the sample (such as beads). In addition, the DNA recovered after lysis using the method of the invention can be directly analysed (i.e. without a purification step) using conventional molecular biology techniques such as Polymerase Chain Reaction (PCR) or electrophoresis. Finally, release is obtained without degradation of the nucleic acids of the species.

According to other embodiments of the method of the invention:

step A) may consist of providing a device according to characteristic (ix) above, step C) of sliding the piston in the chamber until the first and second walls are in lysis position and step D) of rotating the piston so that these walls remain in contact with each other;

step A) may consist of providing a device according to (x) above, step B) of placing a liquid containing the species to be lysed between the walls, step C) of sliding the piston inside the chamber until the liquid has been filtered through the microporous wall and only these species remain on the microporous wall, these walls being in lysis position, and step D) of rotating the piston so that these walls remain in contact with each other;

step A) may consist of providing a device according to (xi) above, step B) of inletting a liquid containing the species to be lysed via the fluid inlet between these walls, step C) of sliding the piston in the chamber until these walls are in lysis position, step D) of rotating the piston so that these walls remain in contact with each other and step F) of circulating an eluting liquid between the fluid inlet and outlet to recover the lysate through this outlet; and step A) may consist of providing a device according to (xii) above, step B) of inletting a liquid containing the species to be lysed via the fluid inlet between the impervious membrane and the second wall, step C) of sliding the piston inside the chamber until these walls are in lysis position via the membrane, step D) of rotating the piston so that these walls remain in contact with each other via the membrane, and step F) of circulating an eluting liquid between the fluid inlet and the fluid outlet to recover the lysate through the fluid outlet.

Other characteristics of the invention will be set forth in the following detailed description given with reference to the appended Figures which respectively illustrate:

FIGS. 1 and 2, two cross-sectional schematic views of a first embodiment of a cell lysis device according to the invention, FIG. 3, a cross-sectional schematic view of a second embodiment of a cell lysis device according to the invention;

FIG. 4, a cross-sectional schematic view of a third embodiment of a cell lysis device according to the invention;

FIG. 5, a cross-sectional schematic view of a fourth embodiment of a cell lysis device according to the invention;

In the description, the following terms are defined as follows.

Rough surface: a surface having an average surface roughness parameter Ra, corresponding to the arithmetic average of Ra parameter measurements, higher than 0.2 µm, preferably between 0.2 µm and 10 µm, more preferably between 0.2 µm and 3 µm (the average surface roughness parameter or coefficient Ra is determined using a profilometer as detailed below);

Microporous: this concerns a wall or layer of material comprising sufficiently large open pores to allow the passing of liquids such as water, but sufficiently small to prevent the passing of biological species to be lysed and the biological material derived from lysis that is to be analysed. Typically, a microporous wall in the meaning of the invention comprises open pores having a diameter of less than 1 µm, and preferably less than 0.2 µm. For example, mention can be made of sintered filters, filters in porous silica, ceramic filters and porous polymer or porous metal filters;

Macroporous: this concerns a wall or layer or material comprising open pores or channels sufficiently large to allow the passing of liquids such as water, but also sufficiently large to allow the passing of biological species to be lysed or the biological material derived from lysis that is to be analysed. Typically, a macroporous wall in the meaning of the invention comprises open pores or channels having a diameter larger than 0.2 µm and preferably larger than 1 µm. For example, mention can be made of a layer of glass, of metal or polymer provided with channels crossing through the layer;

Biological species: in particular cells, microorganisms, particularly bacteria, spores, viruses, fungi, microalgae.

To conduct lysis of biological species such as microorganisms, cells, spores etc., the invention proposes a mechanical lysis device comprising a first wall and a second wall mounted movable relative to one another, between an initial position in which the first and second walls are drawn apart, and a lysis position in which the first wall presses against the second wall.

The first and second walls are also mounted movable relative to one another under shear in the lysis position i.e. one pressing on the other. Shear can be obtained by rotation or translation of the first wall in relation to the second wall. The invention therefore makes provision for two degrees of freedom between the walls: one degree of freedom to draw the walls into contact with each other, and one degree of freedom to allow shear when the walls bear upon one another.

According to the invention, at least one among the first and second walls has a rough bearing surface bearing against the other wall. In other words, the rough surface has an average surface roughness parameter Ra of between 0.2 µm and 10 µm, preferably between 0.2 µm and 3 µm.

As an example of bearing pressure, tests were conducted using a ground glass slide and a conventional glass slide held between the thumb and index of a hand. Mere finger force applied with pressure and shear is sufficient to obtain lysis of the species placed between the two slides.

Figures 1, 2, 3, 4, 5:
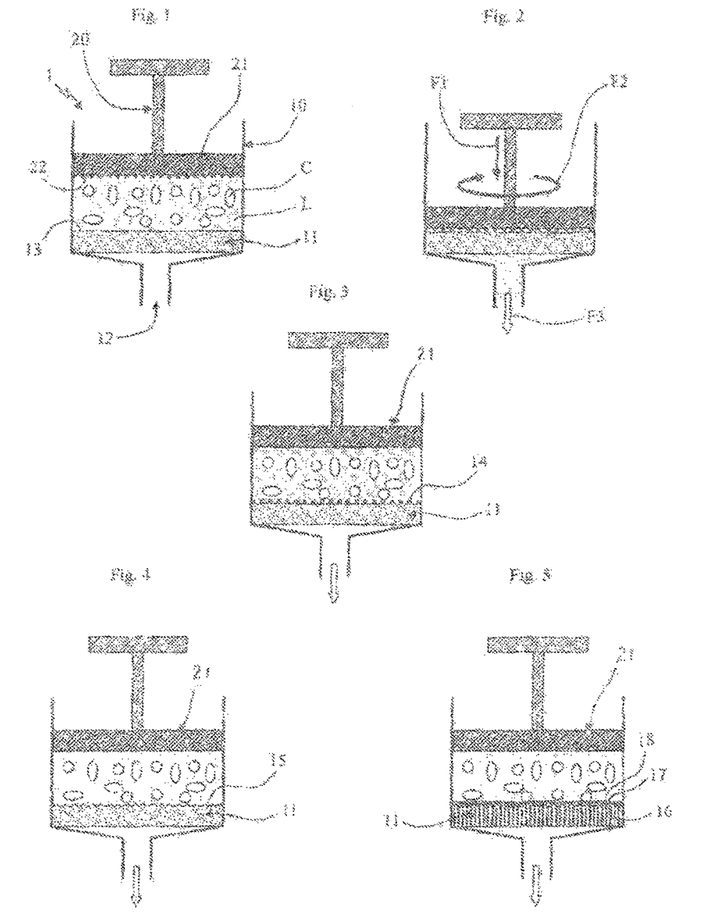

One first embodiment of a device according to the invention is illustrated in FIGS. 1 and 2.

In FIG. 1, the device of the invention is in initial position wherein the first and second walls are drawn apart.

The mechanical lysis device 1 comprises a chamber 10 and a piston 20 mounted mobile in translation inside the chamber 10 between the initial position (FIG. 1) and the lysis position (FIG. 2). A seal (not illustrated) is provided between the piston and the chamber to ensure imperviousness. The first wall 21 is mounted on the mobile piston 20 and the second wall 11 is arranged facing the first wall 21.

In this embodiment, the second wall 11 is microporous to allow the liquid L containing the cells C to be lysed to diffuse through the second wall 11 when the piston 20 is lowered as far as the lysis position in which the two walls 11 and 21 are in contact with each other (FIG. 2). The second wall is a porous filter in polymer for example. Advantageously, the chamber 10 also comprises a fluid outlet 12 arranged opposite the first wall 21 relative to the second microporous wall 11, allowing evacuation of the liquid and of the lysed species. In one alternative, not illustrated, a tank can replace the fluid outlet to receive the liquid.

The microporous wall 11 has a mean pore diameter of between 0.2 µm and 0.5 µm. The diameter of the pores is adapted to ensure that the liquid diffuses through the wall 11, but that the intact cells (i.e. before lysis) remain on the surface of the wall on the surface on which they are lysed. The biological material to be analysed (DNA, proteins, etc.) released by lysis can pass through the filter or remain on the surface of the filter to be recovered.

In the embodiment illustrated in FIGS. 1 and 2, it is the wall 21 carried by the piston 20 which has a rough bearing surface 22 against the other wall. In other words, the microporous wall 11 has a non-rough surface 13 whereas the non-microporous wall 21 has a rough surface 22 e.g. an abrasive surface.

Alternatively, as illustrated in FIG. 3, it is the microporous wall 11 against which a rough surface 14 is arranged. For example, the rough microporous wall 11 is formed of a layer 11 of microporous material having a planar surface 13 on which there is positioned a rough layer 14 intended to press against the wall 21 of the piston 20 in lysis position. In this embodiment, the rough layer 14 must be able to allow passing of the liquid, containing the cells to be lysed.

For example, a rough layer 14 can be used having a thickness of 500 µm to 2 mm, and a microporous layer 11 having a thickness of 500 µm to 5 mm. The rough layer 14 is formed of an abrasive porous material e.g. a wire mesh.

FIG. 4 illustrates an alternative embodiment of a rough microporous wall 11.

In this embodiment, the rough microporous wall 11 is formed of a layer of microporous material having a rough surface 15. In other words, the roughness of the surface 15 is obtained by micro-structuring a microporous material. This layer 11 of microporous material may also be formed of an abrasive filter such as a sintered filter, porous silica, ceramic, porous polymer. For example, it is a filter in stainless steel in the form of a mesh.

Irrespective of the embodiment illustrated in FIGS. 1 to 4, the microporous wall 11 allows the retaining of biological species to be lysed, whilst allowing the biological liquid to flow. After the lysis operation, the lysed biological species flow through the microporous wall 11.

FIG. 5 illustrates a fourth alternative embodiment of a rough microporous wall 11.

In this embodiment, the rough microporous wall 11 is formed of a macroporous layer 16 having a rough surface 17, and of a microporous layer 18 positioned on the macroporous layer 16 and intended to bear against the first wall 21 carried by the piston 20 in lysis position.

The microporous layer 18 must be sufficiently flexible and thin to follow the contour of the roughness of the surface 17 of the macroporous layer 16 in lysis position, so that the roughness of the macroporous layer 16 shows through the microporous layer 18 and the cells can be lysed. By means of the microporous layer 18, the biological species to be lysed are retained and can be lysed.

Figure 6:
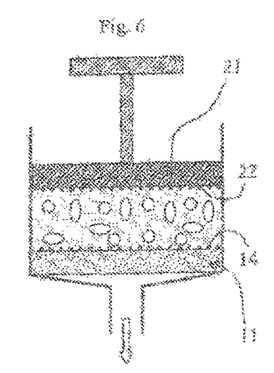
FIG. 6, a cross-sectional schematic view of a fifth embodiment of a cell lysis device according to the invention.

FIG. 6 illustrates a fifth embodiment wherein the first wall 21 and the second wall 11 are both rough i.e. they both have a rough surface 22-14. They may be formed of a combination of the embodiments in FIGS. 1 and 3, a combination of the embodiments in FIGS. 1 and 4 or a combination of the embodiments in FIGS. 1 and 5.

Figure 7:
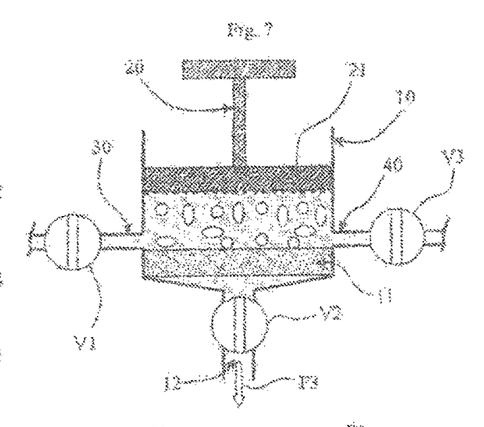
FIGS. 7 and 8, two cross-sectional schematic views of a sixth embodiment of a cell lysis device according to the invention.
Figure 8:
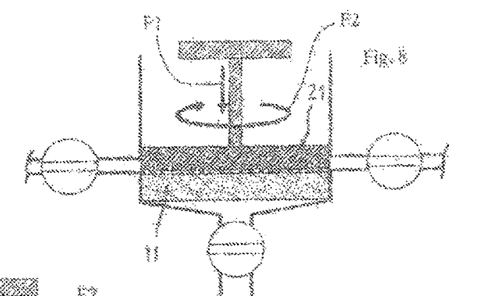

FIGS. 7 and 8 illustrate a sixth embodiment allowing facilitated implantation of lysis and recovery of the biological material to be analysed.

In this embodiment, the chamber 10 also comprises a fluid inlet 30 and a fluid outlet 40 arranged, in cross-sectional view, between the first and second walls 21-11 when they are in initial position.

In initial position, liquid L comprising cells C to be lysed enters the chamber 10 between the first wall 21 and the second wall 11, by opening the valve V1 of the fluid inlet 30 and closing the valves V2 and V3 respectively of the fluid outlets 12 and 40. This step allows placing of the biological cells C to be lysed between the first and second walls 21-11.

Once the chamber 10 is filled with liquid, the valve V1 is closed and valve V2 is open. The piston 20 is then brought to lysis position in the direction of arrow F1 (FIG. 8). The liquid is able to flow through the microporous wall 11 and to be evacuated along arrow F3 through the fluid outlet 12 arranged opposite the first wall 21 relative to the second microporous wall 11.

Therefore, only the biological cells C to be lysed remain on the microporous wall 11.

Once the piston 20 carrying the first wall 21 bears against the second microporous wall 11 in lysis position, the piston 20 is set in rotation in the direction of arrow F2 to generate shear between the first and second walls 21 and 11 and cause mechanical lysis of the biological cells to obtain a lysate. Throughout this step, illustrated in FIG. 8, the valves V1, V2 and V3 remain closed. The first and second walls 21 and 11 are then drawn away from each other until they reach their initial position by lifting the piston 20 in the chamber 10 in the opposite direction of arrow F1.

It is then possible to recover the lysate of biological cells.

In the embodiment in FIGS. 7 and 8, this recovery is obtained by opening the valves V1 and V3 and circulating an eluting liquid between the fluid inlet 30 and outlet 40 to collect the lysed biological material. The cleaning liquid comprising the lysate is then recovered through the fluid outlet 40.

The fluid outlet 40 can have a direct fluid connection with analysis equipment.

All these operations can be carried out in a closed impervious circuit preventing any contamination of the lysate. No beads have to be recovered from the lysate as in current methods. In addition, there is no risk that the recovered biological material may be damaged by chemical products, ruptured by ultrasound or broken down by heat.

The shearing of the biological cells between two walls, at least one of which is rough, allows lysis within a few seconds using a simple, compact, low-cost device.

Figure 9:
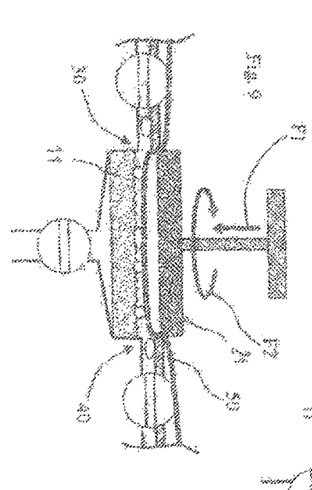
FIG. 9, a cross-sectional schematic view of a seventh embodiment of a cell lysis device according to the invention.

FIG. 9 illustrates a seventh embodiment which avoids having to clean the piston after each lysis.

In this embodiment, the chamber also comprises an impervious membrane 50 arranged between the first wall 21, the fluid inlet 30 and fluid outlet 40. The membrane must be sufficiently thin and flexible so that, in lysis position, it can follow the contour of the roughness of the rough wall that may be carried by the piston and/or chamber.

For example, a polymer film can be used or plastic film having a thickness of between 50 µm and a few hundred µm, e.g. 100 µm, the rough microporous wall possibly being a filter in stainless steel.

After lysis, the piston can be recovered without having to be cleaned and the chamber can be either cleaned for a following lysis or discarded.

This solution can be envisaged through the possibility of integrating the device of the invention in a system of «lab-on-a-chip» type. The chamber is then formed in the chip by the space located between the fluid inlet, the fluid outlet and the second rough wall.

In this case, the use of a membrane and of an added-on piston allows lysis to be performed on a disposable chip, the lysate to be recovered and the chip discarded. The membrane can be washed or discarded and the piston is recovered without having to be washed for subsequent use on another consumable.

Evidently, it is understood that the term «piston» in this case covers any part able to apply mechanical shearing of the cells against the wall of the chamber, this part not necessarily having the conventional form of a piston. As a result, it is the membrane which ensures imperviousness and not the piston which may therefore be in any form.

Figure 10:
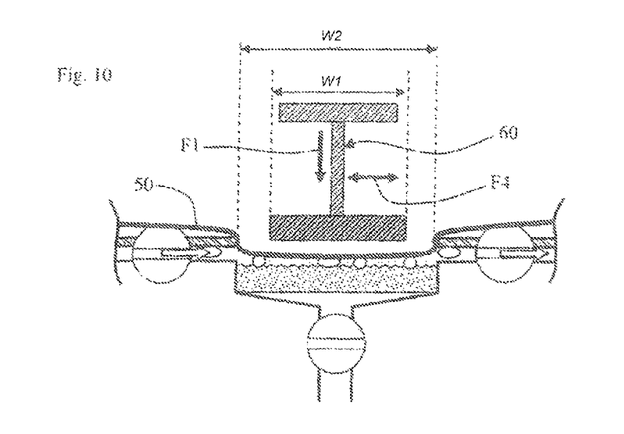
FIG. 10, a cross-sectional schematic view of an eighth embodiment of a cell lysis device according to the invention.

For example, it could be a metallic spatula applied under shear by the user or an automatic screwdriver. The term «automatic screwdriver» designates a piston 60 having an upper part and a lower part such that when the upper part follows translational movement, the lower part of the piston follows rotational movement when resistance opposes its translation. The use of such a device is illustrated in FIG. 10 in which the dimensions of the piston 60 (here the width W1 in cross-sectional view) are smaller than the same dimensions (here the width W2 in cross-sectional view) of the chamber, so that shearing is not necessarily obtained by rotation of the piston 60 but may also be obtained by translation as illustrated by the arrow F4.

Figure 11:
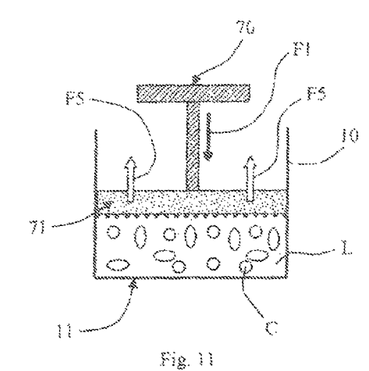
FIGS. 11 and 12, two cross-sectional schematic views of a ninth embodiment of a cell lysis device according to the invention.
Figure 12:
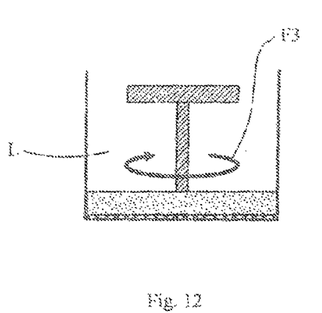

FIGS. 11 and 12 illustrate another embodiment in which it is the piston 70 which has a microporous wall 71. Therefore, when it is lowered in lysis position against the second wall 11 (smooth or rough) of the chamber 10, the liquid L diffuses through the microporous wall 71 of the piston 70 in the direction of arrows F5, and can be evacuated for example by upending the chamber 10 or by aspirating the liquid L. This embodiment can also be combined with a chamber having a fluid inlet and outlet (not illustrated).

The device and method of the invention allow very rapid lysis of biological species to be obtained, without necessitating the need for additional lysis means in the lysis chamber (bead, chemical reagent, application of heat, ultrasound, etc.).

Implementation is simple and can be performed manually or automatically.

In addition to being rapid, the method of the invention is more efficient than the reference method (Precellys© grinder (Bertin)).

The efficiency of lysis is determined indirectly by the amount of DNA released after lysis. This amount of DNA is evaluated using «q-PCR»

The species in contact with a rough surface are subjected to shear and pressure forces using either a non-rough surface such as the surface of a metallic spatula or a pipette tip in plastic, or using a second rough surface (ground glass slide on ground glass).

The species are ground for a time of 2 seconds to release at least one of the cell constituents in the medium (DNA, RNA, protein . . . ).

For example, the method was tested in the following configurations:
- ground glass (Ra=0.425 µm)/biological cells/ground glass (Ra=0.425 µm);
- tip of plastic pipette (Ra non-measurable)/biological cells/ground glass (Ra=0.425 µm);
- flat metallic spatula (Ra≤0.2 µm)/polymer film/biological cells/ground glass (Ra=0.425 µm) on which a porous polymer film was applied e.g. a «Cyclopore Polycarbonate» filter of porosity 0.4 µm marketed by Whatman (reference) and film-coated;
- PMMA ground by sanding (Ra=0.92 µm)/biological cells/ground PMMA (Ra=0.92 µm);
- tip of plastic pipette (Ra non-measurable)/biological cells/ground PMMA (Ra=0.92 µm);
- flat metallic spatula (Ra=0.2 µm)/plastic film/biological cells/ground PMMA (Ra=0.92 µm).

The use of the plastic film is intended to prevent contamination of the species when using a steel spatula.

It is to be noted that:
- two types of ground glass (Ra=0.425 µm; Ra=1.98 µm) were tested;
- the method was validated on species known to be difficult to lyse such as Bg spores (*Bacillus globigii*), Bs (*Bacillus subtilis*);
- lyses were performed dry or else in a volume of 0.5 µL to 5 µL of aqueous solution;
- lyses were performed on a number of spores of between 100 and $10^5$ spores per lysis.

Each roughness parameter Ra was determined as follows: measuring a raw profile using a «Talysur» profilometer; determining a primary profile by applying form removal to the raw profile;
determining a roughness profile by applying a roughness filter to the primary profile;
determining the Ra parameter from said roughness profile.

A first series of tests was intended to compare the efficacy of the method of the invention (two variants: glass-on-glass, and glass-on-plastic) with the reference Precellys method by Bertin. The amount of released DNA after lysis of the spores was evaluated by «q-PCR» using a «Stratagene» machine (Agilent) calibrated in accordance with the manufacturer's instructions.

The results of the first variant were the following:
1. Using «PCR» on the spores lysed with Precellys (Bertin), a Cycle Threshold (Ct) of 31 was obtained.
2. The method of the invention was applied to the same spore solution in the glass-on-glass variant i.e. the spores were lysed between two ground glass slides of Ra=0.425 μm. «PCR» on the spores lysed with the method of the invention gave a Ct of 30, indicating that the concentration of lysed spores was twice higher than in the preceding test.
3. Direct «PCR» was performed on a non-lysed control and a Ct of 35.5. was obtained (most of the spores were not lysed in the initial solution).

The results of the second variant were the following:
1. Using «PCR» on spores lysed with Precellys (Bertin) a Ct of 30 was obtained.
2. The method of the invention was applied to the same spore solution in the variant of glass-on-plastic pipette tip i.e. the spores were lysed between a glass slide of Ra=0.425 μm and a plastic pipette tip. «PCR» on the spores lysed with the method of the invention led to a Ct of 29, indicating that the concentration of lysed spores was twice higher than in the preceding test.
3. Using direct «PCR» on a non-lysed control, a Ct of 36 was obtained (most spores were not lysed in the initial solution).

These results show that:
1. the method of the invention leads to lysis of spores (Ct=30 or 29 against 35.5 or 36 for the control). There is a difference of at least 5 Ct between the solution lysed with the method of the invention and the non-lysed solution, which corresponds to a ratio of $2^5$.
2. that the method is more efficient than the reference lysis method: ΔCt=1 (30-31 and 29-30) i.e. the method of the invention allows the recovery of twice more material.

The objective of a second series of tests was to control the non-adsorption and non-degradation of DNA by the surfaces involved in the method of the invention.

A comparison was made between:
1. Direct «PCR» performed on a solution of pure DNA+ spores, with the obtaining of a Ct of 31; and
2. «PCR» performed on a solution of pure DNA+spores subjected to lysis conforming to the method of the invention in the variant of glass-on-plastic pipette tip, the Ct obtained being 31.

These results show that «PCR» on the solution of pure DNA+spores gives the same results as when the solution has been subjected to the method of the invention. As a result:
1. The method does not destroy DNA.
2. There is no adsorption of DNA by the surfaces.
3. The recovery of the samples is efficient (no losses since same Ct).

The invention claimed is:
1. A device for the mechanical lysis of a biological species contained in a fluid, comprising:
a first wall and a second wall mounted movable relative to one another between an initial position in which the first and second walls are drawn apart and a lysis position in which the first wall presses against the second wall, the first and second walls also being mounted movable under shear relative to one another in the lysis position, wherein at least one of the first and second walls has a rough bearing surface against the other wall and has an average surface roughness parameter Ra of between 0.2 μm and 10 μm, or between 0.2 μm and 3 μm.
2. The mechanical lysis device according to claim 1, wherein one of the first and second walls is a microporous wall porous to liquids and non-porous to the biological species to be lysed.
3. The mechanical lysis device according to claim 2, wherein the microporous wall has a mean pore diameter of less than 1 μm, or less than 0.2 μm.
4. The mechanical lysis device according to claim 2, wherein the microporous wall is rough.
5. The mechanical lysis device according to claim 4, wherein the rough microporous wall is formed of a layer of microporous material having a planar surface on which a rough layer is positioned intended to press against the other wall in the lysis position.
6. The mechanical lysis device according to claim 4, wherein the rough microporous wall is formed of a layer of microporous material having a rough surface.
7. The mechanical lysis device according to claim 4, wherein the rough microporous wall is formed of a layer of macroporous material having a rough surface on which a macroporous layer is positioned intended to press against the other wall in the lysis position, the microporous layer being sufficiently thin and flexible to follow the contour of the surface roughness of the layer in the macroporous material in the lysis position.
8. The mechanical lysis device according to claim 2, wherein the microporous wall is not rough and has an average surface roughness parameter Ra of less than 0.1 μm, whereas the other and non-microporous wall is rough and has an average surface roughness parameter Ra of between 0.2 μm and 10 μm, preferably between 0.2 μm and 3 μm.
9. The mechanical lysis device according to claim 4, wherein the first wall and the second wall are rough.
10. The mechanical lysis device according to claim 1, further comprising a chamber and a piston mounted mobile in the chamber between the initial position and the lysis position, the first wall being mounted on the mobile piston and the second wall being arranged facing the first wall.
11. The mechanical lysis device according to claim 10, wherein the second wall is microporous porous to liquids and non-porous to the biological species to be lysed, and wherein the chamber also comprises a fluid outlet arranged opposite the first wall relative to the second microporous wall.
12. The mechanical lysis device according to claim 11, wherein the chamber also comprises a fluid inlet and another fluid outlet.
13. The mechanical lysis device according to claim 12, wherein the chamber also comprises an impervious membrane arranged between the first wall, the fluid inlet and fluid outlet, the membrane being sufficiently thin and flexible to follow the contour of the roughness of at least one among the first and second walls in the lysis position.

14. A method for the mechanical lysis of a biological species comprising the following steps:
- A) Providing a device for the mechanical lysis of a biological species contained in a fluid, comprising a first wall and a second wall mounted movable relative to one another between an initial position in which the first and second walls are drawn apart and a lysis position in which the first wall presses against the second wall, the first and second walls also being mounted movable under shear relative to one another in the lysis position, wherein at least one of the first and second walls has a rough bearing surface against the other wall and has an average surface roughness parameter Ra of between 0.2 µm and 10 µm, or between 0.2 µm and 3 µm so that the first and second walls lie in the initial position;
- B) Placing the biological species to be lysed between the first and second walls;
- C) Bringing the first and second walls to the lysis position;
- D) Generating shear between the first and second walls in the lysis position to cause mechanical lysis of the biological species and to obtain a lysate;
- E) Drawing the first and second walls apart until they reach the initial position; and
- F) Recovering the lysate of the biological species.

15. The method for mechanical lysis of a biological species according to claim 14, wherein:
- at step A) the device further comprises a chamber and a piston mounted mobile in the chamber between the initial position and the lysis position, the first wall being mounted on the mobile piston and the second wall being arranged facing the first wall;
- at step C) the piston is caused to slide inside the chamber until the first and second walls are in the lysis position; and
- at step D) the piston is rotated so that the first and second walls remain in contact with each other.

16. The method for mechanical lysis of a biological species according to claim 15, wherein:
- at step A) the second wall is microporous porous to liquids and non-porous to the biological species to be lysed, and the chamber also comprises a fluid outlet arranged opposite the first wall relative to the second microporous wall;
- at step B) a liquid containing the biological species to be lysed is placed between the first and second walls;
- at step C) the piston is caused to slide inside the chamber until the liquid has been filtered through the microporous wall, solely the biological species to be lysed are left remaining on the microporous wall and the first and second walls are in the lysis position; and
- at step D) the piston is rotated so that the first and second walls remain in contact with each other.

17. The method for mechanical lysis of a biological species according to claim 16, wherein:
- at step A) the chamber also comprises a fluid inlet and another fluid outlet;
- at step B) the liquid containing the biological species to be lysed is caused to enter through the fluid inlet between the first and second walls;
- at step C) the piston is caused to slide inside the chamber until the first and second walls are in the lysis position;
- at step D) the piston is rotated so that the first and second walls remain in contact with each other; and
- at step F) an eluting liquid is circulated between the fluid inlet and the fluid outlet to recover the lysate through the fluid outlet.

18. The method for mechanical lysis of a biological species according to the preceding claim 17, wherein:
- at step A) the chamber also comprises an impervious membrane arranged between the first wall, the fluid inlet and fluid outlet, the membrane being sufficiently thin and flexible to follow the contour of the roughness of at least one among the first and second walls in the lysis position;
- at step B) a liquid containing the biological species to be lysed is caused to enter through the fluid inlet between the impervious membrane and the second wall;
- at step C) the piston is caused to slide inside the chamber until the first and second walls are in the lysis position via the impervious membrane;
- at step D) the piston is rotated so that the first and second walls remain in contact with each other via the impervious membrane; and
- at step F) an eluting liquid is circulated between the fluid inlet and fluid outlet to recover the lysate through the fluid outlet.

* * * * *